(12) United States Patent
Seal et al.

(10) Patent No.: US 6,605,283 B1
(45) Date of Patent: Aug. 12, 2003

(54) NUCLEOTIDE SEQUENCE FOR THE AVIAN METAPNEUMOVIRUS (COLORADO) ATTACHMENT GLYCOPROTEIN GENE

(75) Inventors: Bruce S. Seal, Athens, GA (US); Rene Alvarez, Crawford, GA (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 10/285,626

(22) Filed: Nov. 1, 2002

(51) Int. Cl.$^7$ ............... A61K 39/155; A61K 39/12; C12P 21/06; C12P 19/34; C12N 15/00
(52) U.S. Cl. ............... 424/211.1; 424/204.1; 424/199.1; 424/186.1; 435/320.1; 435/69.1; 435/91.33; 435/91.1; 435/91.2
(58) Field of Search ............... 424/204.1, 211.1, 424/199.1, 186.1; 435/69.1, 6, 320.1, 91.1, 91.33, 91.2; 536/23.72

(56) References Cited

U.S. PATENT DOCUMENTS

| | | | |
|---|---|---|---|
| 4,559,229 | A | 12/1985 | Page et al. |
| 5,208,023 | A | 5/1993 | Nicholas et al. |
| 6,060,280 | A | 5/2000 | Wertz et al. |
| 6,077,511 | A | 6/2000 | Langedijk |
| 6,086,892 | A | 7/2000 | Cook |
| 6,264,957 | B1 | 7/2001 | Collins |

FOREIGN PATENT DOCUMENTS

| | | | |
|---|---|---|---|
| WO | WO 02/21147 | * | 3/2002 |

OTHER PUBLICATIONS

Alvarez et al , Journal of Clinical Microbiology, Apr. 2003, vol. 41, No. 4, pp. 1730–1735.*
Pastey, M., et al., "Baculovirus Expression of the Fusion Protein Gene of Bovine Respiratory Syncytial Virus and Utility of the Recombinant Protein in a Diagnostic Enzyme Immunoassay", *JCM*, vol. 36, (4), pp. 1105–1108, Apr. 1998.
Shin, H–J., et al., "Avian Pneumovirus (APV) RNA from Wild and Sentinel Birds in the United States has Genetic Homology with RNA from APV Isolates from Domestic Turkeys", *JCM*, vol. 38, (11), pp. 4282–4284, Nov. 2000.
Bayon–Auboyer, M–H., et al., "Nucleotide sequences of the F, L and G protein genes of two non–A/non–B avian pneumoviruses (APV) reveal a novel APV subgroup", *J. General Virology*, vol. 81, pp. 2723–2733, 2000.
Seal, B., "Avian pneumoviruses and emergence of a new type in the United States of America", *Animal Health Res. Reviews*, vol. 1 (1), pp. 67–72, 2000.
Juhasz, K., et al., "Extensive sequence variation in the attachment (G) protein gene of avian pneumovirus: evidence for two distinct subgroups",*J. General Virology*, vol. 75, pp. 2873–2880, 1994.

Giraud, P., et al., "Turkey rhinotracheitis in France: Preliminary investigations on a ciliostatic virus", *The Veterinary Record*, p. 606, Dec. 13, 1986.
Feldman, S., et al., "Identification of a Linear Heparin Binding Domain for Human Respiratory Syncytial Virus Attachment Glycoprotein G", *J. of Virology*, vol. 73, (8), pp. 6610–6617, Aug. 1999.
Ling, R., et al., "Sequence analysis of the 22K, SH and G genes of turkey rhinotracheitis virus and their intergenic regions reveals a gene order different from that of other pneumoviruses", *J. of General Virology*, vol. 73, pp. 1709–1715, 1992.
Cook, J., et al., "Antigenic differentiation of strains of turkey rhinotracheitis virus using monoclonal antibodies", *Avian Pathology*, vol. 22, pp. 257–273, 1993.
Collins, M.S., et al., "Antigenic differentiation of avian pneumovirus isolates using polyclonal antisera and mouse monoclonal antibodies", *Avian Pathology*, vol. 22, pp. 469–479, 1993.
Collins, M.S., et al., "Characterization of a Virus Associated with Turkey Rhinotracheitis", *J. General Virol.*, vol. 69, pp. 909–916, 1988.
Shin, H–J., et al., "Molecular Epidemiology of Subgroup C Avian Pneumoviruses Isolated in the United States and Comparison with Subgroup A and B Viruses", *J. of Clinical Microbiology*, vol. 40, (5), pp. 1687–1693, May 2002.
Juhasz, K., et al., "Extensive sequence variation in the attachment (G) protein gene of avian pneumovirus: evidence for two distinct subgroups",*J. General Virology*, vol. 75, pp. 2873–2880, 1994.
Seal, B., et al., "Fusion protein predicted amino acid sequence of the first US avian pneumovirus isolate and lack of heterogeneity among other US isolates", *Virus Research*, vol. 66, pp. 139–147, 2000.
Li, J., et al., "Sequence of the nucleocapsid protein gene of subgroup A and B avian pneumoviruses", *Virus Research*, vol. 41, pp. 185–191, 1996.
Dar, A., et al., "Sequence analysis of the nucleocapsid and phosphoprotein genes of avian pneumoviruses circulating in the US", *Virus Research*, vol. 79, pp. 15–25, 2001.
Van Den Hoogen, B., et al., "A Newly discovered human pneumovirus isolated from young children with respiratory tract disease", *Nature Medicine*, vol. 7, (6), pp. 719–724, Jun. 2001.
Van Den Hoogen, B., et al., "Analysis of the Genomic Sequence of a Human Metapneumovirus", *Virology*, vol. 295, pp. 119–132, 2002.

* cited by examiner

*Primary Examiner*—Ali R. Salimi
(74) *Attorney, Agent, or Firm*—John D. Fado; Gail E. Poulos

(57) ABSTRACT

The nucleic acid and the corresponding amino acid sequence for the attachment glycoprotein of Avian Metapneumovirus (Colorado) Type C strain is provided. The nucleotide sequence is 1,321 base pairs with only one substantial open reading frame encoding a glycoprotein of about 435 amino acids with a predicted $M_r$ of about 48,483 and a net charge of about 23.15 at neutral pH.

3 Claims, 2 Drawing Sheets

```
GGGACAAGTC AACATGGAGC CCCTGAAAGT CTCTGGAAGT GGAGGGATAC      50
CGATGAAGAC AAGGCTTAAT ATCATACTTG AGAAGTCAAT CAATAAAATC     100
TTGATCATTT TAGGATTACT ATTAACTGCC TCAACTGTAA TTACAATCAC     150
ACTCACAGTG GAGTATATAA GAGTAGAAAA TGAATTGCAA CTTTGCAAGA     200
TGGAAGCAGA GGTGGCCAAG ACAACTCCGG AACCACCAAC ACAGCCAACG     250
AAGACAACTC CTACACTAAC CAGAACCAGA TCAACCACCG CATCCCTCAA     300
AACCAGACCA GTTTCAAGGA CCACTCATCC CACCAATCCC AGCTGCTGGA     350
GAGAGGAGGA AAAGTGCCAG AATATCACAG CTAAATGGTC CAATTGTTTT     400
GGCACATCTC TACCTGTGAG GGTGAACTGC ACGGTACTAA GAGAATTGTG     450
TGATGAGCAG CCAGGCAATC ACACAACAGT TCAAGTATCA AGGAGGTGTA     500
CATGCATATA TGCATTAAAT TGGGATTGTA GTTATGCTTG TGAGAGAGAC     550
TACACTAGCC GACCCTATTG TGGTCCACAG AAAAAGATTA AAAGCATAAA     600
CCAATTTTTT AGTTATTTAA AAATCATGAA TATGTCTGGA CAGTGCCAAG     650
GCCAAGAAAA ACCAACACGA GAACAGGTGA TCCAATGTTT AAAAACGATC     700
AGAGAAGGAA AAACGGGACA AGTCAACATG GAGGTCAAGG TAGAGAATGT     750
TGGCAAGTCA CAGGAGCTTA AAGTCAAAGT CAAGAATTTT ATAAAAAGGT     800
CTGATTGCAA GAAAAAACTT TTTGCCTTGA TTTTAGGGCT AGTCAGCTTT     850
GAACTCACTA TGAATATAAT GCTGTCTGTC ATGTATGTGG AGTCAAATGA     900
GGCCCTAAGT TTATGTAGGA TCCTAGGGAC TCCTGCTCCA AGGGATCATA     950
AGACTAACAC AGAAAACGCA ACAAAGGAAA CAACACTCCA CACAACGACC    1000
ACAACAAGGG ATCCAGAGGT GAGGGAAACA AAAACCACCA AGCCCCAGGC    1050
CAATGAAGGA GCAACAAACC CAAGCAGGAA CCTCACCACC AAGGGAGACA    1100
AACACCAAAC GACAAGAGCA ACAACAGAGG CAGAACTGGA AAAACAAAGC    1150
AAACAAACCA CAGAGCCAGG CCAGCCCCCA AAAGCACACC CCCACAAGAC    1200
CAAGCAGCAA ATCCCCCACC ACAACACAAG CAATAGCACA ACTGACAACA    1250
CCAACAACCC CAAAAGCAAG CACAGCACCC AAGAACAGAC AGGCAACAAC    1300
CAAAAAAACC GAAACGGA TA A                                  1321
```

Fig. 1

SEQUENCE LISTING

<160> NUMBER OF SEQ ID NOS: 4

<210> SEQ ID NO 1
<211> LENGTH: 1321
<212> TYPE: DNA
<213> ORGANISM: Avian Metapneumovirus
<220> FEATURE:
<221> NAME/KEY: CDS
<222> LOCATION: (14)..(1321)
<223> OTHER INFORMATION:

<400> SEQUENCE: 1

```
gggacaagtc aac atg gag ccc ctg aaa gtc tct gga agt gga ggg ata        49
            Met Glu Pro Leu Lys Val Ser Gly Ser Gly Gly Ile
              1               5                  10 ccg atg aag aca agg ctt aat atc ata ctt gag aag tca atc aat aaa        97
Pro Met Lys Thr Arg Leu Asn Ile Ile Leu Glu Lys Ser Ile Asn Lys
         15                  20                  25 atc ttg atc att tta gga tta cta tta act gcc tca act gta att aca       145
Ile Leu Ile Ile Leu Gly Leu Leu Leu Thr Ala Ser Thr Val Ile Thr
     30                  35                  40 atc aca ctc aca gtg gag tat ata aga gta gaa aat gaa ttg caa ctt       193
Ile Thr Leu Thr Val Glu Tyr Ile Arg Val Glu Asn Glu Leu Gln Leu
45                  50                  55                  60 tgc aag atg gaa gca gag gtg gcc aag aca act ccg gaa cca cca aca       241
Cys Lys Met Glu Ala Glu Val Ala Lys Thr Thr Pro Glu Pro Pro Thr
                 65                  70                  75 cag cca acg aag aca act cct aca cta acc aga acc aga tca acc acc       289
Gln Pro Thr Lys Thr Thr Pro Thr Leu Thr Arg Thr Arg Ser Thr Thr
             80                  85                  90 gca tcc ctc aaa acc aga cca gtt tca agg acc act cat ccc acc aat       337
Ala Ser Leu Lys Thr Arg Pro Val Ser Arg Thr Thr His Pro Thr Asn
         95                 100                 105 ccc agc tgc tgg aga gag gag gaa aag tgc cag aat atc aca gct aaa       385
Pro Ser Cys Trp Arg Glu Glu Glu Lys Cys Gln Asn Ile Thr Ala Lys
     110                 115                 120 tgg tcc aat tgt ttt ggc aca tct cta cct gtg agg gtg aac tgc acg       433
```

```
                                                             -continued

Trp Ser Asn Cys Phe Gly Thr Ser Leu Pro Val Arg Val Asn Cys Thr
125                 130                 135                 140 gta cta aga gaa ttg tgt gat gag cag cca ggc aat cac aca aca gtt        481
Val Leu Arg Glu Leu Cys Asp Glu Gln Pro Gly Asn His Thr Thr Val
                145                 150                 155 caa gta tca agg agg tgt aca tgc ata tat gca tta aat tgg gat tgt        529
Gln Val Ser Arg Arg Cys Thr Cys Ile Tyr Ala Leu Asn Trp Asp Cys
            160                 165                 170 agt tat gct tgt gag aga gac tac act agc cga ccc tat tgt ggt cca        577
Ser Tyr Ala Cys Glu Arg Asp Tyr Thr Ser Arg Pro Tyr Cys Gly Pro
        175                 180                 185 cag aaa aag att aaa agc ata aac caa ttt ttt agt tat tta aaa atc        625
Gln Lys Lys Ile Lys Ser Ile Asn Gln Phe Phe Ser Tyr Leu Lys Ile
    190                 195                 200 atg aat atg tct gga cag tgc caa ggc caa gaa aaa cca aca cga gaa        673
Met Asn Met Ser Gly Gln Cys Gln Gly Gln Glu Lys Pro Thr Arg Glu
205                 210                 215                 220 cag gtg atc caa tgt tta aaa acg atc aga gaa gga aaa acg gga caa        721
Gln Val Ile Gln Cys Leu Lys Thr Ile Arg Glu Gly Lys Thr Gly Gln
                225                 230                 235 gtc aac atg gag gtc aag gta gag aat gtt ggc aag tca cag gag ctt        769
Val Asn Met Glu Val Lys Val Glu Asn Val Gly Lys Ser Gln Glu Leu
            240                 245                 250 aaa gtc aaa gtc aag aat ttt ata aaa agg tct gat tgc aag aaa aaa        817
Lys Val Lys Val Lys Asn Phe Ile Lys Arg Ser Asp Cys Lys Lys Lys
        255                 260                 265 ctt ttt gcc ttg att tta ggg cta gtc agc ttt gaa ctc act atg aat        865
Leu Phe Ala Leu Ile Leu Gly Leu Val Ser Phe Glu Leu Thr Met Asn
    270                 275                 280 ata atg ctg tct gtc atg tat gtg gag tca aat gag gcc cta agt tta        913
Ile Met Leu Ser Val Met Tyr Val Glu Ser Asn Glu Ala Leu Ser Leu
285                 290                 295                 300 tgt agg atc cta ggg act cct gct cca agg gat cat aag act aac aca        961
Cys Arg Ile Leu Gly Thr Pro Ala Pro Arg Asp His Lys Thr Asn Thr
                305                 310                 315 gaa aac gca aca aag gaa aca aca ctc cac aca acg acc aca aca agg       1009
Glu Asn Ala Thr Lys Glu Thr Thr Leu His Thr Thr Thr Thr Thr Arg
            320                 325                 330 gat cca gag gtg agg gaa aca aaa acc acc aag ccc cag gcc aat gaa       1057
Asp Pro Glu Val Arg Glu Thr Lys Thr Thr Lys Pro Gln Ala Asn Glu
        335                 340                 345 gga gca aca aac cca agc agg aac ctc acc acc aag gga gac aaa cac       1105
Gly Ala Thr Asn Pro Ser Arg Asn Leu Thr Thr Lys Gly Asp Lys His
    350                 355                 360 caa acg aca aga gca aca aca gag gca gaa ctg gaa aaa caa agc aaa       1153
Gln Thr Thr Arg Ala Thr Thr Glu Ala Glu Leu Glu Lys Gln Ser Lys
365                 370                 375                 380 caa acc aca gag cca ggc cag ccc cca aaa gca cac ccc cac aag acc       1201
Gln Thr Thr Glu Pro Gly Gln Pro Pro Lys Ala His Pro His Lys Thr
                385                 390                 395 aag cag caa atc ccc cac cac aac aca agc aat agc aca act gac aac       1249
Lys Gln Gln Ile Pro His His Asn Thr Ser Asn Ser Thr Thr Asp Asn
            400                 405                 410 acc aac aac ccc aaa agc aag cac agc acc caa gaa cag aca ggc aac       1297
Thr Asn Asn Pro Lys Ser Lys His Ser Thr Gln Glu Gln Thr Gly Asn
        415                 420                 425 aac caa aaa aac cga aac gga taa                                       1321
Asn Gln Lys Asn Arg Asn Gly
    430                 435
```

```
<210> SEQ ID NO 2
<211> LENGTH: 435
<212> TYPE: PRT
<213> ORGANISM: Avian Metapneumovirus

<400> SEQUENCE: 2

Met Glu Pro Leu Lys Val Ser Gly Ser Gly Gly Ile Pro Met Lys Thr
1               5                   10                  15

Arg Leu Asn Ile Ile Leu Glu Lys Ser Ile Asn Lys Ile Leu Ile Ile
            20                  25                  30

Leu Gly Leu Leu Leu Thr Ala Ser Thr Val Ile Thr Ile Thr Leu Thr
        35                  40                  45

Val Glu Tyr Ile Arg Val Glu Asn Glu Leu Gln Leu Cys Lys Met Glu
    50                  55                  60

Ala Glu Val Ala Lys Thr Thr Pro Glu Pro Pro Thr Gln Pro Thr Lys
65                  70                  75                  80

Thr Thr Pro Thr Leu Thr Arg Thr Arg Ser Thr Thr Ala Ser Leu Lys
                85                  90                  95

Thr Arg Pro Val Ser Arg Thr Thr His Pro Thr Asn Pro Ser Cys Trp
            100                 105                 110

Arg Glu Glu Lys Cys Gln Asn Ile Thr Ala Lys Trp Ser Asn Cys
        115                 120                 125

Phe Gly Thr Ser Leu Pro Val Arg Val Asn Cys Thr Val Leu Arg Glu
    130                 135                 140

Leu Cys Asp Glu Gln Pro Gly Asn His Thr Thr Val Gln Val Ser Arg
145                 150                 155                 160

Arg Cys Thr Cys Ile Tyr Ala Leu Asn Trp Asp Cys Ser Tyr Ala Cys
                165                 170                 175

Glu Arg Asp Tyr Thr Ser Arg Pro Tyr Cys Gly Pro Gln Lys Lys Ile
            180                 185                 190

Lys Ser Ile Asn Gln Phe Phe Ser Tyr Leu Lys Ile Met Asn Met Ser
        195                 200                 205

Gly Gln Cys Gln Gly Gln Glu Lys Pro Thr Arg Glu Gln Val Ile Gln
    210                 215                 220

Cys Leu Lys Thr Ile Arg Glu Gly Lys Thr Gly Gln Val Asn Met Glu
225                 230                 235                 240

Val Lys Val Glu Asn Val Gly Lys Ser Gln Glu Leu Lys Val Lys Val
                245                 250                 255

Lys Asn Phe Ile Lys Arg Ser Asp Cys Lys Lys Leu Phe Ala Leu
            260                 265                 270

Ile Leu Gly Leu Val Ser Phe Glu Leu Thr Met Asn Ile Met Leu Ser
        275                 280                 285

Val Met Tyr Val Glu Ser Asn Glu Ala Leu Ser Leu Cys Arg Ile Leu
    290                 295                 300

Gly Thr Pro Ala Pro Arg Asp His Lys Thr Asn Thr Glu Asn Ala Thr
305                 310                 315                 320

Lys Glu Thr Thr Leu His Thr Thr Thr Thr Arg Asp Pro Glu Val
                325                 330                 335

Arg Glu Thr Lys Thr Thr Lys Pro Gln Ala Asn Glu Gly Ala Thr Asn
            340                 345                 350

Pro Ser Arg Asn Leu Thr Thr Lys Gly Asp Lys His Gln Thr Thr Arg
        355                 360                 365

Ala Thr Thr Glu Ala Glu Leu Glu Lys Gln Ser Lys Gln Thr Thr Glu
    370                 375                 380
```

-continued

```
Pro Gly Gln Pro Pro Lys Ala His Pro His Lys Thr Lys Gln Gln Ile
385                 390                 395                 400

Pro His His Asn Thr Ser Asn Ser Thr Thr Asp Asn Thr Asn Asn Pro
                405                 410                 415

Lys Ser Lys His Ser Thr Gln Glu Gln Thr Gly Asn Asn Gln Lys Asn
            420                 425                 430

Arg Asn Gly
        435

<210> SEQ ID NO 3
<211> LENGTH: 24
<212> TYPE: DNA
<213> ORGANISM: Avian Metapneumovirus

<400> SEQUENCE: 3
aacatggagc ccctgaaagt ctct                                          24

<210> SEQ ID NO 4
<211> LENGTH: 23
<212> TYPE: DNA
<213> ORGANISM: Avian Metapneumovirus

<400> SEQUENCE: 4
tttttggttg ttgcctgtct ctt                                           23
```

NUCLEOTIDE SEQUENCE FOR THE AVIAN METAPNEUMOVIRUS (COLORADO) ATTACHMENT GLYCOPROTEIN GENE

BACKGROUND OF THE INVENTION

1. Field of the Invention

The present invention relates to recombinant DNA molecules for the attachment glycoprotein gene of the avian Metapneumovirus (Colorado) (APV/CO) as well as to the corresponding protein and peptides derived therefrom. The invention further relates to the production and use of the DNA and glycoprotein in diagnostics and for vaccine production.

2. Description of the Related Art

Avian Metapneumovirus (APV) causes turkey rhinotracheitis (TRT) and is associated with swollen head syndrome (SHS) of chickens that is usually accompanied by secondary bacterial infections that increase mortality. Clinically, the disease is similar to *Bordetella avium* infection and is primarily respiratory in turkeys. There is loss of egg production in laying flocks. In chickens, APV infections may be subclinical, without development of SHS. The virus was first reported in South Africa during the early 1970s and virus were subsequently isolated in Europe, Israel, and Asia (Alexander, In: Diseases of Poultry, , 10$^{th}$ edition, Calnick B W, Barnes H J, McDougall L R, Saif Y M, and Beard C W (eds), Iowa State University Press, 541–569, 1997); Jones, Avian Pathology, 25, 639–648, 1996). During February 1997, APV was officially isolated by the National Veterinary Services Laboratory (NVSL, APHIS, USDA) from commercial turkeys in Colorado (APV/CO) following an outbreak of TRT the previous year. During the first 10 months of the U.S. outbreak it was not possible to detect virus serologically due to the lack of cross-reactivity of the United States (US) APV isolate with reagents produced in Europe. An ELISA was developed by NVSL using inactivated purified APV/CO as an antigen and serological evidence of APV infection was subsequently demonstrated in turkey flocks in the north-central United States of America (USA). In the USA mortality due to APV infections in turkeys ranges from 0 to 30% when accompanied by bacterial infections with condemnations due to airsacculitis (Senne et al., In: Proceedings, 134$^{th}$ Annual Conference, Schaumburg Illinois American Veterinary Medical Association, page 190, 1997). Absence of serologic reactivity of APV/CO-infected birds with APV serotypes A and B isolates and genomic sequence diversity clearly demonstrated emergence of new strains of this virus previously been considered exotic to North America.

The clinical signs in birds infected with APV are primarily respiratory and includes reales, sneezing and nasal discharge (Alexander, 1997 and Jones, 1996, supra). Viral antigen is primarily detected among experimentally infected chickens and turkey poults in the cilia of turbinate, tracheal and lung epithelial cells (Majo et al., Avian Diseases, 39, 887–896, 1995; Veterinary Microbiology, 52, 37–48, 1996; and Veterinary Microbiology, 57, 29–40, 1997). The presence of APV in the lungs proves that the virus is capable of infecting the lower respiratory tract. Extensive replication of APV in the turbinates causes severe rhinitis that allows infection by secondary bacterial agents (Jones et al., Avian Pathology, 17, 841–850, 1988; Majo et al., 1997 supra). Viral genomic RNA can be detected by ELISA or serum neutralization for several weeks after infection of adult turkeys (Jones et al, 1988, supra).

The diagnosis of APV infection has been accomplished primarily by the isolation of virus from clinical samples or the detection of virus-specific antibodies in serum. Primary isolation of APV is performed by viral replication in tracheal organ culture from specific pathogen-free chicken or turkey embryos (Wyeth and Alexander, IN: A Laboratory Manual of the Isolation and Identification of Avian Pathogens, 3$^{rd}$ edition, Pruchase H G, Arp L H, Domermuth C H, and Pearson J E (eds), Kennet Square, Pa.: American Association of Avian Pathologists, 121–123, 1989). However, the United States virus was isolated using chicken embryo fibroblast cells in culture (Senne et al, supra). Virus neutralization assays, immunofluorescence, and ELISA have been used for the serologic detection of antibodies to APV (Grant et al, Veterinary Record, 120, 279–280, 1987; O'Loan et al., Journal of Virological Methods, 25, 271–282, 1989).

An ELISA was used to search for antibodies to APV among chickens and turkeys in Canada (Heckert et al., Veterinary Record, 132, 172, 1993), using antigen from an APV strain from Europe. Because the current North American APV/CO isolate is not cross-reactive with European isolates, these sera should be evaluated again with a more appropriate antigen.

The presence of viral nucleic acids can be established by a reverse transcription-polymerase chain reaction (RT-PCR) method using oligonucleotide primers specific for the fusion protein gene of APV type A (Jing et al., Avian Pathology, 22, 771–783, 1993). However, an RT-PCR protocol using primers from within the APV nucleocapsid protein gene may prove more useful for detecting different viral subtypes (Bayon-Auboyer et al., Archives of Virology, 144, 10901–1109, 1999).

Vaccination with live, attenuated, cell cultured-adapted APV strains has been used to control disease caused by APV (Jones, 1996 supra; Jones et al., Veterinary Record, 119, 599–600, 1986). Currently, APV type A vaccines protect against challenge from type A and B viruses from Europe (Cook et al., Veterinary Record, 136, 392–393, 1995; Avian Pathology, 25, 231–243, 1996), although maternal antibody fails to protect pouts from challenge (Naylor et al., Avian Diseases, 41, 968–971, 1997). Use of live virus vaccine followed by inactivated vaccines provided protection against both respiratory infection and reduced egg production in turkeys (Cook et al., 1996, supra). There are no published reports demonstrating whether these vaccines will protect against disease caused by the United States isolate. Also, prototype live attenuated APV vaccines may cause disease in young poults that is apparently due to virulent viral subpopulations that must be removed from current vaccine preparations (Naylor and Jones, Vaccine 12, 1225–1230, 1994). A fowlpox virus recombinant containing the F protein gene conferred only a partial protective immune response to APV challenge (Qingzhong et al., Vaccine, 12, 569–573, 1994). Cyclophosphamide treatment of poultry to suppress B-cell responses before APV vaccination, still resulted in only a partial response to challenge. It was concluded that cellular immune responses maybe more important than humoral responses in vaccination with APV (Jones et al., Research in Veterinary Science, 53, 38–41, 1992).

Pneumovirus are members of the family Paramyxoviridae and contain a non-segmented, single-strand, negative-sense RNA genome of approximately 15 kilobases in length. Viruses related to APV include the human, bovine, ovine and caprine respiratory synitial viruses, and pneumonia virus of mice as well as the recently identified human Metapneumovirus (van den Hoogen et al., Nat. Med., Volume 7(6), 719–724, 2001). Pneumoviruses generally encode ten genes versus the six or seven of other paramyxoviruses, such as Newcastle disease virus (NDV). These include genes for the non-structural proteins (NS1 and NS2), nucleoprotein (N), phosphoprotein (P), matrix protein (M), small hydrophobic protein (SH), surface glycoprotein (G), fusion protein (F), second matrix protein (M2), and a viral RNA-dependent RNA polymerase (L). The pneumoviruses have an F protein that promotes cell fusion, these viruses do not hemagglutinate, nor do they have neuraminidase activity in their G attachment protein. This is an important distinguishing characteristic from the other paramyxoviruses (Collins et al., In: Field's Virology, 3$^{rd}$ edition, Fields B N, Knipe D M, and Howley P M (eds), Philadelphia: Lippincott-Raven, 1313–1351, 1996).

Classification of European APV isolates was initially based on the molecular characterization of the virion (Collins et al., Veterinary Record, 119, 606, 1986; Collins and Gough, Journal of General Virology, 69, 909–916, 1988); electrophoretic mobility of viral proteins (Ling and Pringle, Journal of General Virology, 69, 917–923, 1988) and number of MRNA species detected in virus-infected cells (Cavanaugh and Barrett, Virus Research, 11, 241–256, 1988). Sequence information for the N (Li et al., Virus Research, 41, 185–191, 1996), P (Ling et al., Virus Research, 36, 247–257, 1995), M (Randhawa et al., Journal of General Virology, 77, 3047–3051, 1996; Yu et al., Virology, 186, 426–434, 1992), M2 (Yu et al., Journal of General Virology, 73, 1355–1356, 1992), SH (Ling et al., Journal of General Virology, 73, 1709–1715, 1992), G (Juhasz and Easton, Journal of General Virology, 75, 2873–2880, 1994; Ling et al., 1992, supra), and L (Randhawa et al., supra) protein genes is now published for several European APV isolates. The sequence in every case is most similar to other members of the Pneumovirus genus. The putative gene order of APV (3'-N-P-M-F-M2-SH-G-L-5') is different from its mammalian counterpart (3'-NS1-NS2-N-P-M-SH-G-F-M2-L-5'), wherein the SH and G genes are located 5' to the M2 gene (Ling et al., 1992, supra). The extreme 3' and 5' ends of one European APV isolate's genome were determined which established that the NS1 and NS2 genes are absent in the avian viruses (Randhawa et al., Journal of Virology, 71, 9849–9854, 1997). This is different from their mammalian counterparts and along with its smaller L gene, results in APV having a genome of only 13.3 kilobases (Randhawa et al., 1996b, supra). Since APV has no NS1 or NS2 gene, but has an M2 gene; with structural characteristics like those of other pneumoviruses, it has become the type of virus of a new genus within the metapneumovirus (Pringle, Archives of Virology, 141, 2251–2256, 1996).

The G gene of APV encodes the surface glycoprotein (cell attachment protein) protein and serves as one of the major antigenic determinants of pneumoviruses. On the basis of the nucleotide sequence and the predicted amino acid sequence of the G protein gene, two APV subgroups, designated A and B, have been identified (Juhasz and Eastoh, 1994, supra). The group A viruses included isolates from the UK and France, while group B viruses included isolates from Spain, Italy, and Hungary. However, Type B are now found in the UK (Naylor et al., Avian Pathology, 26, 327–338, 1997a). The G proteins are 98.5–99.7% similar among groups, but only 38% similar between the two APV clusters. This correlates with earlier data demonstrating that various APV isolates were antigenically similar but could be separated serologically into two separate groups (Collins et al., Avian Pathology, 22, 469–479, 1993; Cook et al., Avian Pathology 22, 257–273, 1993). This relationship was confirmed by sequence analysis of the F protein gene (Naylor et al., Journal of General Virology, 79, 1393–1398, 1998) and the more conserved M gene (Randhawa et al, Virus Genes, 12, 179–183 1996a). This difference in viral proteins could account for discrepancies found when different antigens were used for serology (Eterradossi et al., Veterinary Record, 131, 563–564, 1992).

The M protein gene is highly conserved among paramyxoviruses (Rima et al., In: Genetics and Pathogenicity of Negative Strand Viruses, Kolakofsky D, and Maby B M J (eds), 254–263, 1989) and can be reliably used for molecular epidemiology (Seal et al., Virus Research, 66, 1–22, 2000a). The predicted M proteins of European APV type A and B isolates share 89% identity in their amino acid sequence. However, the predicted M protein of APV/CO shares only 78% identity with APV type A and 77% with APV type B protein sequences. The US isolate is phylogenetically separate from the European APV type A and B strains, which cluster together. Sequence information for the APV/CO M protein gene and the predicted amino acid sequence of the M protein confirm the unique nature of this isolate compared with its European counterparts (Seal, Virus Research, 58, 45–52, 1998).

More recently, the F protein gene sequence of the Colorado virus and several isolates from Minnesota have been reported (Seal et al, Virus Research, 66, 139–147, 2000b). The predicted amino acid sequence of the F protein of the US APV isolate shared approximately 71.5% sequence identity with that of the European APV types. In contrast, the European type A and B viruses shared 83% of their F protein predicted amino acid sequences with and were phylogenetically separate from the US viruses. Variation in the F protein was extensive in the first ten amino acids and the last 50 carboxy-terminal residues of the F protein (Seal et al., 2000b, supra). Cleavage of the F protein into a larger F1 and a smaller F2 protein mediates cell fusion and is necessary for the spread of the virus (Collins et al., 1996, supra). The amino-terminal portion of F1 is presumed to be involved in membrane fusion and is highly conserved among all three APV types (Naylor et al, 199, supra; Seal et al., 2000b, supra)

The cleavage site sequence of the fusion protein is highly variable among the three APV types, and codon usage for the shared amino acids is not consistent among them at these residues (Seal et al., 2000b, supra). The US isolates have a fusion protein sequence of Arg-Lys-Ala-Arg compared with Arg-Arg-Arg-Arg for the type A isolates and Arg-Lys-Lys-Arg for the type B viruses. Cleavage of the paramyxovirus F proteins required for the replication of these virus type (Nagai, Microbiology and Immunology, 39, 1–9, 1995) occurs by the action.of cellular proteases that recognize the sequence Arg-X-Arg/Lys-Arg-Arg (Hosaka et al., Journal of Biological Chemistry, 266, 12127–12130, 1991). The Ala residue present in the F cleavage site sequence of the US APV isolates but not in APV types A and B may affect their relative virulences. This could explain the lack of ciliostasis in tracheal organ cultures among US viruses (Cook et al., Avian Pathology, 28, 607–617, 1999). Also, it is possible that bacterial proteases (Akaike et al., Journal of Virology, 63, 2252–2259, 1989) play a role in F protein cleavage because severe disease is associated with secondary bacterial infections (Majo et al., 1997, supra).

The origin of the US virus and how APV emerged in North America is unknown. Viruses isolated in South America are reported to be of the APV type A (Dani et al., Avian Pathology, 28, 473–476, 1999a; Dani et al., Journal of Virological Methods, 79, 237–241, 1999b; Toro et al., Avian Diseases, 42, 815–817, 1998). Monospecific antisera and neutralizing monoclonal antibodies to APV types A and B do not neutralize the US virus and vice versa (Cook et al., 1999, supra). However, hyperimmune sera to type A virus can partially neutralize the US virus, whereas type B hyperimmune sera does not. Also, vaccination of birds with the US virus reduces signs of disease after challenge with the APV type A but not type B (Cook et al., 1999, supra). The APV isolate from the US is phylogenetically separate from the A and B types on the basis of the nucleotide sequences of the M and F amino acid coding sequences. There are fewer sequence differences between the type A virus and the US isolate than between the B type and the US isolate. It is conceivable that the US viruses could have the A type virus as a progenitor. However, the absolute distances from the A or B types to the US virus are substantial and the US virus is phylogenetically separate from the other types with very high bootstrap confidence limits. The APV isolates from the US are serologically distinct from type A and B viruses (Cook et al., 1999, supra; Senne et al., 1997, supra), and this relationship has been confirmed by sequence analysis of the genes for the M (Seal, 1998, supra) and F (Seal et al, 2000b, supra).

While various avian pneumoviruses are known to cause upper respiratory disease in avians, there remains a need for methods for detecting different strains of avian pneumoviruses in avians, especially poultry, which overcome some of the limitations of related art detection methods. The present invention described below is a novel nucleic acid encoding the Avian Metapneumovirus (Colorado) type C attachment glycoprotein DNA, a novel attachment glycoprotein and peptides derived therefrom encoded by the type C attachment glycoprotein gene, vaccines produced using said DNA, and immunodiagnostics for detecting type C avian Metapneumovirus.

SUMMARY OF THE INVENTION

It is, therefore, an object of the present invention to provide a novel nucleotide sequence encoding Avian Metapneumovirus (Colorado) Type C strain attachment glycoprotein.

A further object of the present invention is to provide an amino acid sequence for Avian Metapneumovirus Type C strain attachment glycoprotein.

Another object of the present invention is to provide methods for detecting Avian Metapneumovirus (Colorado) type C strain in animals, especially poultry using antibodies, primers, or probes produced from the novel nucleotide sequence and/or amino acid sequence for avian Metapneumovirus (Colorado) Type C strain attachment glycoprotein.

A still further object of the present invention is to provide a vaccine using the type C strain glycoprotein and/or the type C strain glycoprotein nucleic acid sequence.

Further objects and advantages of the present invention will become apparent from following description.

Deposit of Virus

A plasmid containing the G attachment glycoprotein gene of avian metapneumovirus (Colorado) has been deposited under the provisions of the Budapest Treaty with the American Type Culture Collection (P.O. Box 1549, Manassas, Va. 20108 USA) on The Accession Number is ATCC

BRIEF DESCRIPTION OF THE DRAWINGS

FIG. 1 is the cDNA nucleotide sequence for Avian Metapneumovirus (Colorado) Type C strain attachment glycoprotein.

DETAILED DESCRIPTION OF THE INVENTION

Figure 2:
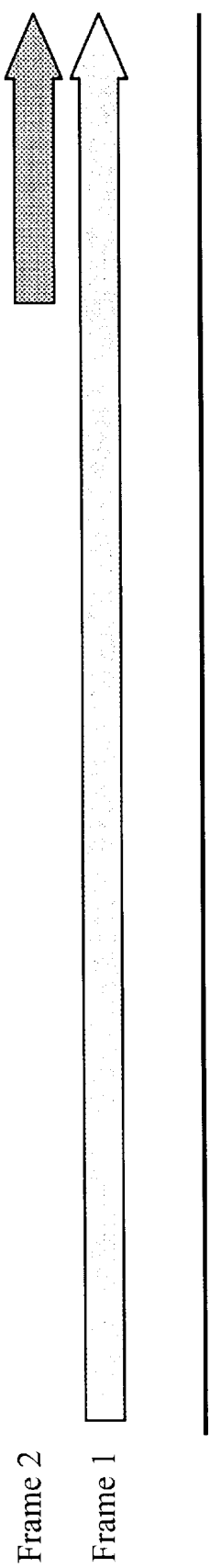
FIG. 2 is a universal ORF Map for Avian Metapneumovirus (Colorado) Type C strain attachment glycoprotein.

The present invention provides an isolated nucleic acid (SEQ. ID NO 1 and FIG. 1) and isolated glycoprotein (SEQ ID NO 2) and their sequences for the cell attachment glycoprotein of Avian Metapneumovirus (Colorado) (APV/CO) type C determined by sequencing cloned cDNAs of intracellular mRNA. The invention also provides a nucleic acid capable of selectively hybridizing DNA, RNA, and cDNA sequences which can be derived from SEQ ID NO 1. While SEQ ID No. 1 is a DNA sequence, the invention also includes the corresponding RNA sequence. The nucleotide sequence comprises 1,321 base pairs with only one substantial open reading frame (FIG. 2), nucleotide 14 to 1,321, encoding a protein of about 435 amino acids, with a predicted $M_r$ of about 48,483 and a net charge of about 23.15 at neutral pH. A second putative leader sequence was identified at position 715–723 followed by a second putative open reading frame spanning positions 728–1321, encoding a protein of about 197 amino acid residues with a $M_r$ of about 22,024 and a net charge of about 11.20 at neutral pH.

Analysis of the attachment protein by BLAST (Atschul et al, Nucleic Acid Res., Volume 25(17), 3389–3402, 1997) revealed two mucin-like motifs encompassing amino acid positions 21 to 163 and 190 to 433 with potential transmembrane regions within these areas from residues 24 to 45 and 266 to 287.

Comparison of the protein sequence (SEQ ID NO 2) of the present invention with that of avian pneumoviruses types A, B, and non A-non B as well as human respiratory syncytial virus (hRSV) revealed overall amino acid identities ranging from about 4 to about 16.5%.

The Avian Metapneumovirus (Colorado) (APV/CO) attachment glycoprotein gene is defined as a nucleic acid sequence encoding Avian Metapneumovirus (Colorado) attachment glycoprotein according to the invention by cloning cDNA transcripts of APV mRNA and identifying clones containing full length attachment glycoprotein-encoding sequences, or alternatively, by identifying APV attachment glycoprotein-encoding nucleic acid sequences using probes having SEQ ID NO 3 and 4. The invention provides an isolated APV/CO attachment glycoprotein nucleic acid comprising the nucleotide sequence set forth in SEQ ID NO 1 (FIG. 1), as well as allelic variants or homologs. The nucleic acids can be single or double stranded, and can be DNA or RNA depending on the purpose for which it is intended. The novel attachment glycoprotein nucleotide sequence of this invention also can be characterized as a sequence that shares at least about 60% identity with the sequence of SEQ ID NO 1. In preferred embodiments, the attachment glycoprotein nucleotide sequence of this invention can be characterized as an attachment glycoprotein nucleotide sequence that shares at least about 70%, 80%, or 90% identity with the sequence of SEQ ID NO 1. For purposes of the present invention, the term "isolated" is defined as separated from other nucleic acids found in naturally occurring organisms. The recitation "capable of selectively hybridizing" is defined as a sequence which does not hybridize with other nucleic acids to prevent adequate positive hybridization with the nucleic acid for avian Metapneumovirus (Colorado) Type C strain attachment glycoprotein. The term "avian" is defined as any bird which may be infected with avian Metapneumovirus (Colorado) Type C strain including, for example, turkeys, chickens, geese, ducks, ostrich, emu, pheasant, etc.

cDNA containing the complete open reading frame for the APV/CO attachment glycoprotein mRNA may be synthesized using APV/CO mRNA template and a specific synthetic nucleotide for second strand synthesis. The nucleotide sequence for the oligonucleotide may be determined from sequence analysis of APV/CO mRNA. First strand synthesis may be performed as described in D'Allessio et al. (Focus 9, 1–4, 1987). Following synthesis, the RNA template may be digested with Rnase A (at least about 1 µg/µl) for about 30 minutes at about 37° C. The resulting single-stranded cDNAs may then be isolated by phenol extraction and ethanol precipitation. The oligonucleotide used for second strand synthesis should preferably have a sequence specific for the 5' end of the APV/CO attachment glycoprotein mRNA, and may also, contain a useful restriction endonuclease cleavage site to facilitate cloning. The single stranded cDNAs may then be mixed with oligonucleotide (at about 50 µg/ml), heated to about 100° C. for approximately 1 minute, and placed on ice. Reverse transcriptase may then be used to synthesize the second strand of the cDNAs in a reaction mixture which may comprise about 50 mM Tris-HCl (approximately pH 8.0), about 50 mM KCl, about 5 mM MgCl$_2$, about 10 mM dithiothreitol, about 1.6 mM dNTPs, and about 100 U reverse transcriptase, incubated for approximately one hour at about 50° C. The cDNAs may then be separated from protein by phenol extraction, recovered by ethanol precipitation, and ends made blunt with T4 DNA polymerase. Blunt-ended cDNAs may then be digested with an appropriate restriction endonuclease (for example, which recognizes a cleavage site in the oligonucleotide primer but not within the protein-encoding sequence), separated from protein by phenol extraction, and then cloned into a suitable vector.

Alternatively, cDNAs generated from viral mRNA may be cloned into vectors, and clones carrying the nucleic acid sequences for APV/CO attachment glycoprotein may be generated using, as probes, oligonucleotides containing nucleotide sequences from SEQ ID NO: 1. Viral CDNA libraries may be screened, for example, using the method set forth in Grunstein and Hogness (Proc. Natl. Acad. Sci. USA 72, 3961–3965, 1975). Retrieved clones may then be analyzed by restriction-fragment mapping and sequencing techniques well known in the art (e.g., Sanger et al, Proc. Natl. Acad. Sci. USA, 72, 3918–3921, 1979). Alternatively, the APV/CO attachment glycoprotein may be synthesized chemically based on SEQ ID NO: 4.

Additional APV/CO attachment glycoprotein nucleic acids of this invention can be identified by probing viral cDNA transcribed from mRNA viruses isolated from diseased animals, obtained as herein described. Samples for testing include, for example, intestines, bursa, thymus, feces, spleen, kidney, pancreas, nasal swabs, tracheal swabs, and isolates from any upper tract mucosal surface. Samples can also include litter from infected houses and biological vectors such as, for example, darkling beetles. One method for detection is the use of polymerase chain reaction amplification which can be used to detect other APV/CO attachment glycoprotein cDNAs of the invention by transcribing mRNA followed by amplifying pneumoviral specific cDNA sequences. mRNA can be extracted using any method established in the prior art for extracting RNA. For purposes of the present invention, total RNA can be obtained by methods and/or kits well established in the art such as, for example, TRIzol® Total RNA Isolation Reagent (Life Technologies™, Rockville, Md.), Rneasy (Qiagen), Oligotex RNA kit, Qiamp viral RNA kit, etc. Repeated cycles of denaturation, primer annealing and extension carried out with polymerase, e.g. a heat stable Taq polymerase, lead to exponential increases in the concentration of desired DNA sequences. Using cDNA sequences of APV/CO attachment glycoprotein nucleic acid as disclosed herein, synthetic oligonucleotides or primers can be prepared which are complementary to the ends of sequences which are to be amplified. The sample cDNA obtained from transcribed MRNA of virus isolated from diseased animals can be denatured at high temperatures (e.g. 95° C.) and then reannealed in the presence of a large molar excess of the primers. The primers, oriented with their 3' ends pointing towards each other, hybridize to opposite strands of the target sequence and prime enzymatic extension along the nucleic acid template in the presence of the four deoxyribonucleotide triphosphates. The end product is then denatured again for another cycle. After this three-step cycle has been repeated several times, amplification of a DNA segment by more than one million-fold can be achieved.

Primers chosen for the PCR amplification should be at least approximately 10 nucleotides in length and amplifying a product at least approximately 30 nucleotides in length. The length and G+C content of the primers are used to determine the melting temperature ($T_m$) according to formulas known in the art. The $T_m$ establishes the temperature at which primer annealing to the sample nucleic acid is performed. For primers shorter than 20 nucleotides, an estimate of $T_m$ can be calculated as $T_m=4(G+C)+2(A+T)$, while for longer primers, an estimate of the $T_m$ requires the use of the nearest neighbor calculations, which takes into account thermodynamic parameters and is embedded in most available computer programs for designing PCR primers (see, e.g. Dieffenbach, C S et al.1995 General concepts for PCR primer design, IN: PCR Primer. A Laboratory Manual; Dieffenbach and Dueskler, eds., Cold Spring Harbor Laboratory Press, Plainview, N.Y.).

Detection of the amplified product can be by any of several standard methods, such as electrophoresis on an agarose of polyacrylamide gel and any intercalating agents such as for example, Syler green, acridine orange, ethidium bromide, etc. for staining in order to visualize the nucleic acids on the gel using ultraviolet light. For purposes of the present invention, any technique known in the art can be used for detecting the amplified product. Each test includes a positive APV/CO control and a negative noninfected control sample.

Avian Metapneumovirus (Colorado) strain C cell attachment glycoprotein genes with significant homology, i.e. sequence identity, to nucleic acid SEQ ID NO: 1 can readily be obtained by screening collected samples from animals suspected of being infected with Avian Metapneumovirus (Colorado) strain C with a probe comprising one or more nucleic acid sequences contained in SEQ ID NO: 1, SEQ ID NO: 3, or SEQ ID NO: 4. Nucleic acid samples collected from said infected animals that specifically hybridize with such a probe under relatively high-stringency conditions (e.g. low salt concentrations and/or high temperatures of hybridization) can be processed for the isolation of an Avian Metapneumovirus (Colorado) cell attachment glycoprotein gene of this invention according to the procedures described herein.

As is known in the art, annealing reactions (between primers or probes and the sample RNA or DNA) are affected by the concentration, sequence complexity, base composition, and length of the primer/probe; the concentration of monovalent cations; the presence of hybrid destabilizing agents (e.g. formamide); and the incubation temperature. The following formula relates may of these parameters to the $T_m$ (the temperature at which half of the DNA molecules have dissociated into single strands): $T_m$=81.5° C.+16.6 log M+41(mole fraction of G+C)−(550/L)−0.62(% formamide), where M is the concentration of monovalent cations and L is the molecular length of the probe in bases. Increasing the salt concentration from 100 mM to 1 M increases the $T_m$ by 16° C. Annealing temperatures that are 25° C. below the $T_m$ of the native DNA or cDNA usually provide the maximum rate of hybridization. For example, for genomic DNAs, the annealing temperature is typically 65° C. in aqueous solvents containing 250 mM Na$^+$. Adding formamide to a final concentration of 50% lowers the annealing temperature to 42° C. In general, the higher the probe concentration, the more rapid the annealing reaction. However, the competing reaction of probe strands reannealing to each other will also occur more rapidly. For this reason, probe concentrations need to be relatively low (≦10 ng/ml hybridization solution). Alternatively, single-stranded probes can be used.

Stringency, or the degree to which mismatches are permitted in the binding of two single strands, is a critical parameter in all annealing reactions and is affected by salt concentration and annealing temperature. The $T_m$ of a duplex decreased by approximately 1° C. for each 1% of mismatched base pairs, except for short DNA (15–30 bases), for which each mismatch can reduce the $T_m$ by 5° C. (Wolff, R and Gemmill, R 1997 Purify and Analyzing genomic DNA IN: Genome Analysis-A Laboratory Manual, Vol. 1; Virren, B et al., eds., Cold Spring Harbor Laboratory Press, Plainview, N.Y.). The higher the salt concentration, the greater the number of mismatches that can be tolerated at a given temperature. The final stringency of the reaction can then be readily adjusted by using a series of post-hybridization washes of increasing stringency. The specific hybridization signal should be assessed by autoradiography between these washes and compared with background.

The present invention additionally provides an isolated APV/CO attachment glycoprotein nucleic acid that hybridizes under stringent conditions with a nucleic acid set forth in SEQ ID NO: 1. Such hybridizing nucleic acids can be fragments of the complementary strands for the referenced sequence or can be primers or probes that can identify the referenced sequences.

In a specific embodiment, the invention provides an isolated nucleic acid encoding the APV/CO attachment glycoprotein comprising the amino acid sequence set forth in SEQ ID NO:2.

The present invention additionally provides an isolated APV/CO attachment glycoprotein encoded by a nucleic acid of this invention. Isolated means substantially free from the naturally occurring materials with which the glycoprotein is normally associated in nature. The isolated glycoprotein need not be homogeneous, but must be sufficiently free of contaminants to be useful in research and commercial applications, for example, for use in detecting or preparing antibodies to the glycoprotein, or in screening libraries of molecules for those molecules that interact with the glycoprotein. The attachment glycoprotein can be readily obtained by any of several means. For example, the nucleotide sequence encoding the attachment glycoprotein can be translated and then the corresponding attachment glycoprotein, or any portion thereof, can be synthesized mechanically by standard methods. Additionally, the nucleic acids encoding the attachment glycoprotein can be expressed or synthesized, an antibody specific for the resulting attachment glycoprotein can be raised by standard methods (see, e.g., Harlow and Lane, Antibodies: A Laboratory Manual, Cold Spring Harbor, N.Y., 1988), and the attachment glycoprotein can be isolated by selective binding with the antibody. Such attachment glycoproteins can be purified to the extent desired by standard methods of protein purification (see, e.g., Sambrook set al., Molecular Cloning: A Laboratory Manual, 2$^{nd}$ Edition, Cold Spring Harbor Laboratory, Cold Spring Harbor, N.Y., 1989). The APV/CO attachment glycoprotein can be isolated and purified by standard methods including chromatography such as ion exchange, affinity and sizing column chromatography for example, centrifugation, differential solubility, or by other standard techniques for the purification of proteins. The antibodies so produced can be used as diagnostic tools for the presence of the virus.

As will be appreciated by those skilled in the art, the invention also includes those APV/CO attachment glycoproteins having slight variations in amino acid sequences or other properties. Amino acid substitutions can be selected by known parameters to be neutral (see, e.g., Robinson W E Jr., and Mitchell W M., AIDS, 4:S151–S162, 1990). Such variations may arise naturally as allelic variations (e.g. due to genetic polymorphism) or may be produced by human intervention (e.g. by mutagenesis of cloned DNA sequences), such as induced point, deletion, insertion, and substitution mutants. Minor changes in amino acid sequence are generally preferred, such as additions or deletions at the ends of molecules. Substitutions may be designed based on, for example, the model of Dayhoff, et al., (in Atlas of Protein Sequence and Structure 1978, Nat'l Biomed. Res. Found., Washington D.C.). These modifications can result in changes in the amino acid sequence, provide silent mutations, modify a restriction site, or provide other specific mutations. Likewise, such amino acid changes result in a different nucleic acid encoding the APV/CO attachment glycoprotein. Thus, alternative nucleic acids are also contemplated by such modifications.

The nucleotide sequence coding for APV/CO attachment glycoprotein, or a portion thereof, can be inserted into an appropriate expression vector, i.e., a vector which contains the necessary elements for the transcription and translation of the inserted glycoprotein-coding sequence. Examples of expression vectors include, but are not limited to, human or animal viruses such as vaccinia virus, adenovirus, insect viruses such as baculovirus, yeast vectors, bacteriophage vectors such as lambda, and plasmid and cosmid DNA vectors. The necessary transcriptional and translation signals can also be supplied by the native APV/CO gene. A variety of host-vector systems may be utilized to express the glycoprotein-coding sequence. These include but are not limited to mammalian cell systems infected with virus (e.g., vaccina virus, adenovirus, etc.); insect cell systems infected with virus (e.g., baculovirus); microorganisms such as yeast containing yeast vectors, or bacteria transformed with bacteriophage DNA, plasmid DNA, or cosmid DNA. The expression elements of these vectors vary in their strengths and specificities. Depending on the host-vector system utilized, any one of a number of suitable transcription and translation elements may be used.

For example, for yeast expression, there are several advantages. First, proteins produced in yeast expression systems exhibit correct disulfide bonding. Second, post-translational glycosylation is efficiently carried out by yeast secretory systems. The Saccharomyces cerevisiae pre-pro-alpha factor leader region (encoded by the Mfα-1 gene) is routinely used to direct protein secretion from yeast. The leader region of pre-pro-alpha factor contains a signal peptide and a pro-segment which includes a recognition sequence for yeast protease encoded by the KEX 2 gene; this enzyme cleaves the precursor protein on the carboxyl side of a Lys-Arg dipeptide cleavage signal sequence. The protein or peptide coding sequence can be fused in-frame to the pre-pro-alpha factor leader region. This construct is then put under the control of a strong transcription promoter such as the alcohol dehydrogenase I promoter or a glycolytic promoter. The protein or peptide coding sequence is followed by a translation termination codon which is followed by transcription termination signals. Alternatively, the protein or peptide coding sequences can be fused to a second protein coding sequence, such as Sj26 or β-galactosidase, used to facilitate purification of the fusion protein by affinity chromatography. The insertion of protease cleavage sites to separate components of the fusion protein is applicable to constructs used for expression in yeast.

In another example, mammalian cells permit the expression of proteins in an environment that favors important post-translational modifications such as folding and cysteine pairing, addition of complex carbohydrate structures, and secretion of active protein. Vectors useful for the expression of protein or peptide in mammalian cells are characterized by insertion of the protein or peptide coding sequence between a strong viral promoter and a polyadenylation signal. The vectors can contain genes conferring selection markers such as antibiotic resistance, examples of which include gentamicin, methotrexate, tetracycline, hygromycin, resistance for use as a selectable marker to permit detection and/or selection of those cells transformed with the desired nucleic acid sequences (See U. S. Pat. No. 4,740,362; herein incorporated by reference). The coding sequence can be inserted into a cell line using an antibiotic-resistance-encoding vector. Presence of the vector DNA in transformed cells can be confirmed by Southern analysis and production of a cDNA or opposite strand RNA corresponding to the protein or peptide coding sequence can be confirmed by Northern analysis. A number of other suitable host cell lines capable of secreting intact protein have been developed in the art and include HeLA cells, myeloma cell lines, Jurkat cells, etc. Expression vectors for these cells can include expression control sequences, such as origin of replication, a promoter, an enhancer, and necessary information processing sites, such as ribosome binding sites, RNA splice sites, polyadenylation sites, transcriptional terminator sequences, etc. Preferred expression control sequences are promoters derived from immunoglobulin genes, SV40, Adenovirus, Bovine Papilloma virus, etc.

The vectors containing nucleic acid segments of interest can be transferred into the host cell by well known methods which vary depending on the type of cellular host. For example, calcium chloride transfection is commonly utilized for prokaryotic cells, whereas calcium phosphate treatment or electroporation may be used for other cellular hosts.

Alternate vectors for the expression of proteins or peptides in mammalian cells similar to those developed for the expression of human gamma interferon, tissue plasminogen activator, clotting factor VIII, hepatitis B virus surface antigen, protease Nexin1 and eosinophil major basic protein, also can be employed. Further, the vector can include CMV promoter sequences and a polyadenylation signal available for expression of inserted nucleic acid in mammalian cells (such as for example COS7).

Polynucleotides encoding variant polypeptides may include sequences that facilitate transcription (expression sequences) and translation of the encoding sequences such that the encoded polypeptide product is produced. Construction of such polynucleotides is well known in the art. For example, such polynucleotides can include a promoter, a transcription termination site (polyadenylation site in eukaryotic expression hosts), a ribosome binding site, and optionally, an enhancer for use in eukaryotic expression hosts, and optionally, sequences for replication of a vector.

Any of the methods previously described for the insertion of DNA fragments into a vector may be used to construct expression vectors containing a chimeric gene consisting of appropriate transcriptional/translational control signals and the glycoprotein coding sequences. These methods may include in vitro recombinant DNA and synthetic techniques and in vivo recombinations (genetic recombination). Expression of nucleic acid sequence encoding APV/CO attachment glycoprotein or peptide fragment may be regulated by a second nucleic acid sequence so that the APV/CO attachment glycoprotein or peptide fragment is expressed in a host transformed with the recombinant DNA molecule. For example, expression of APV/CO attachment glycoprotein may be controlled by any promoter/enhancer element known in the art. Promoters which may be used to control APV/CO attachment glycoprotein expression include, but are not limited to the CMV promoter (Stephens and Cockett, Nucleic Acids Research, 17, 7110, 1989);. the SV40 early promoter region (Bernoist and Chambon, Nature, 290, 304–310, 1981); the promoter contained in the 3' long terminal repeat of Rous sarcoma virus (Yamamoto et al., Cell, 22, 787–797, 1980); the herpes thymidine kinase promoter (Wagner et al., Proc. Natl. Acad. Sci. USA, 78, 1441–1445, 1981); the regulatory sequences of the metallothionine gene (Brinster et al., Nature, 296, 39–42, 1982); prokaryotic expression vectors such as p-lactamase promoter (Villa-Kamaroff et al., Proc. Natl. Acad. Sci. USA, 75, 3727–3731, 1978); or the tac promoter (DeBoer et al., Proc. Natl. Acad. Sci. USA, 80, 21–25, 1983), see also "Useful proteins from recombinant bacteria" in Scientific American, 242, 74–94, 1980; plant expression vectors comprising the nopaline synthetism promoter region (Herrera-Estrella et al., Nature, 303, 209–213, 1983); or the cauliflower mosaic virus 35S RNA promoter (Gardner et al., Nucleic Acids Research, 9, 2871, 1981); and the promoter for the photosynthetic enzyme ribulose biphosphate carboxylase (Herrera-Estrella et al., Nature, 310, 115–120, 1984); promoter elements from yeast or other fungi such as the Gal 4 promoter, the ADC (alcohol dehydrogenase) promoter, PGK (Phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., Cell, 38, 639–646, 1984; Ornitz et al., Cold Spring Harbor Symp. Quant. Biol., 50, 399–4409, 1986; MacDonald, Hepatology, 7, 425–515, 1987); insulin gene control region which is active in pancreatic beta cells (Hanahan, Nature, 318, 533–538, 1985; Alexander et al., Mol. Cell. Biol., 7, 1436–1444, 1987), mouse mammary tumor virus control region which is active in testicular, breast, lymphoid and mast cells (Leder et al., Cell, 45, 485–495, 1986), albumin gene control region which is active in liver (Pinkert et al., Genes and Devel., 1, 161–171, 1987), beta-globin gene control region which is active in myeloid cells (Mogram et al., Nature, 315, 338–340, 1985; Kollias et al., Cell, 46, 89–94, 1986); myelin basic protein gene control region which is active in oligodendrocyte cell in the brain (Readhead et al., Cell, 48, 703–712, 1987); myosin light chain-2 gene control region which is active in skeletal muscle (Sani, Nature, 314, 283–286), and gonadotropic releasing hormone gene control region which is active in the hypothalamus (Mason et al., Science, 234, 1372–1378, 1986).

Expression vectors containing the APV/CO attachment glycoprotein gene inserts can be identified by three general approaches: (1) the presence of DNA-DNA hybridization, (2) presence or absence of marker gene functions, and (3)

expression of the inserted sequences. In the first approach, the presence of a foreign gene inserted in an expression vector can be detected by DNA-DNA hybridization using probes comprising sequences that are homologous to the inserted APV/CO attachment glycoprotein gene. In the second approach, the recombinant vector/host system can be identified and selected based upon the presence or absence of certain marker gene functions such as thymidine kinase activity, resistance to antibiotics, transformation, phenotype, occlusion body formation in baculovirus, etc.; caused by the insertion of foreign genes in the vector. For example, if the APV/CO attachment glycoprotein gene is inserted within the marker gene sequence of the vector, recombinants containing the glycoprotein gene insert can be identified by the absence of the marker gene function. In the third approach, recombinant expression vectors can be identified by assaying the foreign gene product expressed by the recombinant.

The present invention also provides cells containing a nucleic acid of the invention. A cell containing a nucleic acid encoding the APV/CO attachment glycoprotein typically can replicate the DNA and, further, typically can express the encoded glycoprotein. The cell can be a prokaryotic cell, particularly for the purpose of producing quantities of the nucleic acid, or a eukaryotic cell, such as Vero or CHO cells (Ausubel et al., In: Current Protocols in Molecular Biology, Greene Publishing Associates and Wiley-Interscience, 1994; Chen et al., Mol. Cell Biol., Volume 7, 2745–2752, 1987; Duzgunes et al., Methods in Enzymol., Volume 221, 303–306, 1993; Wigler et al., Cell, Volume 11, 223–232, 1977) for the purpose of expressing the encoded attachment glycoprotein so that the resultant produced attachment glycoprotein has avian cell-determined processing modifications.

Additionally, a host cell strain may be chosen which modulates the expression of the inserted sequences, or modifies and processes the gene product. Expression from certain promoters can be evaluated in the presence of certain inducers; controlling the expression of the APV/CO attachment glycoprotein. Furthermore, different host cells have characteristic and specific mechanisms for the translational and post-translation processing and modification, such as for example glycosylation and/or cleavage, of proteins. Appropriate cell lines or host systems can be chosen to ensure the desired modification and processing of the foreign protein expressed. For example, expression in a bacterial system can be used to produce an unglycosylated core protein product. Expression in mammalian cells can be used to ensure native glycosylation of the heterologous APV/CO attachment glycoprotein. Furthermore, different vector/host expression systems may effect processing reactions such as proteolytic cleavages to different extents.

Additionally, recombinant viruses which infect but are nonpathogenic in poultry, including but not limited to fowl pox viruses of birds which include turkey herpes virus and infectious laryngotracheitis virus, for example, may be engineered to express APV/CO attachment glycoprotein using suitable promoter elements. Such recombinant viruses may be used to infect poultry and thereby produce immunity to APV/CO. Additionally, recombinant viruses capable of expressing APV/CO attachment glycoprotein, but which are potentially pathogenic, may be inactivated prior to administration as a component of a vaccine.

The APV/CO attachment glycoprotein of the present invention can be used to provide purified antigenic polypeptide fragments encoded by the nucleic acid of the present invention. As used herein, "purified" means the antigen is at least sufficiently free of contaminants or cell components with which the antigen normally occurs to distinguish the antigen from the contaminants or components. Purified antigen and antigenic fragments are also referred herein as the antigen or the APV/CO attachment glycoprotein antigen or the Avian virus (Colorado) attachment glycoprotein. It is contemplated that the antigenic fragments can be encoded from any portion of the nucleic acid encoding the APV/CO attachment glycoprotein of the present invention as set forth in the sequence listing as SEQ ID 1, but especially for fragments encoded by the open reading frame-nucleotides 14 to 1,321.

An antigenic fragment can be isolated from the whole antigen by chemical or mechanical disruption. The purified fragments thus obtained can be tested to determine their antigenicity and specificity by the methods taught herein. An immunoreactive fragment is generally an amino acid sequence of at least about 5 consecutive amino acids derived from the antigen amino acid sequence.

The polypeptide fragments of the present invention can also be recombinant proteins obtained by cloning nucleic acids encoding the polypeptide in an expression system capable of producing the antigenic polypeptide or fragments thereof.

Once the amino acid sequence of the antigen is provided, it is also possible to synthesize, using standard peptide synthesis techniques, peptide fragments chosen to be homologs to immunoreactive regions of the antigen and to modify these fragments by inclusion, deletion, or modification of particular amino acid residues in the derived sequences. Thus, synthesis or purification of an extremely large number of peptides derived from the antigen is possible.

The amino acid sequence of the present invention can be attached to sequences designed to provide some additional property such as solubility for example. The amino acid sequences of the present invention can include one or more substituted amino acids to provide for some additional property such as to remove and/or add amino acids capable of disulfide bonding, to increase its bioactivity, or alter interactions with gastric acidity, for example. In any case, the peptide must possess a bioactive property, such as immunoreactivity, immunogenicity, etc.

The purified polypeptide fragments thus obtained can be tested to determine their immunogenicity and specificity. Briefly, various concentrations of a putative immunogenically specific fragment are prepared and administered to an animal and the immunological response (e.g. production of antibodies or cell mediated immunity) of an animal to each concentration is determined. The amounts of antigen administered depend on the subject, the condition of the subject, the size of the subject, etc. Thereafter, an animal so inoculated with the antigen can be exposed to the virus to test the potential vaccine effect of the specific immunogenic fragment. The specificity of the putative immunogenic fragment can be ascertained by testing sera or other fluids or lymphocytes from the inoculated animal for cross reactivity with other closely related metapneumoviruses.

The present invention may be used to produce safe and effective APV/CO vaccines. According to the invention, the term vaccine is construed to refer to a preparation which elicits an immune response directed toward a component of the preparation. Advantages of the present invention include the capability of producing APV/CO attachment glycoprotein in quantity for use in vaccines or for the generation of antibodies to be used in passive immunization protocols as well as the ability to provide a recombinant virus vaccine which produces immunogenic APV/CO attachment glycoprotein or peptides derived therefrom which are nonpathogenic. These alternatives circumvent the use of modified live APV/CO virus vaccines which may cause exacerbated symptoms in poultry previously exposed to APV/CO.

According to the invention, the APV/CO attachment glycoprotein sequence may be inserted into an appropriate expression system such that the attachment glycoprotein is produced in quantity for use, for example, in subunit vaccines. In specific embodiments, the APV/CO attachment glycoprotein may be expressed, for example, by recombinant baculovirus, vaccinia, pox, herpes viruses, etc., harvested, and then administered as a protein subunit in a suitable pharmaceutical carrier. A pharmaceutically acceptable carrier can comprise saline or other suitable carriers (Arnon, R. (ed) Synthetic Vaccines I, 83–92, CRC Press, Inc., Boca Raton, Fla., 1987).

Alternatively, recombinant virus, including, but not limited to, mammalian and avian adenoviruses, which are nonpathogenic in poultry but which express APV/CO attachment glycoprotein, may be used to infect poultry and thereby produce immunity to APV/CO without associated disease (Oshop et al., Vet. Immunol. Immunopathol., Volume 89, 1, 2002) The production of APV/CO attachment glycoprotein in recombinant virus vaccinated animals, or a portion or derivative thereof, may additionally prevent attachment of virus to cells, and thereby limit infection.

In vaccines which comprise peptide fragments of the APV/CO attachment glycoprotein, it may be desirable to select peptides which are more likely to elicit an immune response (Andersson et al., FEMS Immunol. Med. Microbiol., Volume 29, 247–253, 200; Bastien et al., Vaccine, Volume 17, 832–836, 1999; Belanger et al., FASEB J., Volume 14, 2323–2328, 2000; Chang et al., Vaccine, Volume 20, 328–335, 2001; Hechert et al., Vet. Immunol. Immunopathol., Volume 89, 67, 2002; Power et al., Vaccine, Volume 19, 2345–2351, 2001; Power et al., Virology, Volume 230, 155–166, 1997). For example, the amino acid sequence of the attachment glycoprotein may be subjected to computer analysis to identify surface epitopes using a method such as, but not limited to, that described in Hopp and Woods (PNAS, USA, 2078, 3824–3828, 1981), which has been successfully used to identify antigenic peptides of Hepatitis B surface antigen. It may also be desirable to modify the attachment glycoprotein peptides in order to increase their immunogenicity, for example, by chemically modifying the peptides or by linking the peptides to a carrier molecule.

The vaccines of the invention may be administered, in a pharmaceutical carrier, by a variety of routes, including, but not limited to, nasally, orally, intramuscularly, subcutaneously, or intravenously, in ovo, or via ingestion of genetically modified plants. Immunogenic amounts of the antigen can be determined using standard procedures. Briefly, various concentrations of a putative specific immunoreactive epitope are prepared, administered to an animal, and the immunological response (e.g. the production of antibodies) of the animal to each concentration is determined. Preferably, between about $10^4$ to about $10^9$ infectious units/ml recombinant viruses may be administered in an inoculation. It may be desirable to administer subunit vaccines of the invention together with an adjuvant, for example, but not limited to, Freunds (complete and incomplete), oil-based adjuvants, avian cytokines, and toxin-based adjuvants, etc. Multiple inoculations may be necessary in order to achieve protective and/or long-lasting immunity.

It can be appreciated from the above that the vaccine can be used as a prophylactic or therapeutic modality. Thus, the invention provides methods of preventing, reducing, and/or treating avian metapneumovirus (Colorado) infection and the associated diseases by administering the vaccine to a subject.

In additional embodiments, the APV/CO attachment glycoprotein nucleic acid, protein, or peptide molecules of the invention, may be utilized to develop monoclonal or polyclonal antibodies directed toward APV/CO attachment glycoprotein. For preparation of monoclonal antibodies directed toward the nucleic acid, protein, and/or peptides of APV/CO attachment glycoprotein, any technique which provides for the production of antibody molecules by continuous cell lines in culture may be used. For example, the hybridoma technique originally developed by Kohler and Milstein (Nature, 256, 495–497, 1975).

A molecular clone of an antibody to APV/CO attachment glycoprotein may be prepared by known techniques. Recombinant DNA methodology (Maniatis et al., Molecular Cloning, A Laboratory Manual, Cold Spring Harbor Laboratory, Cold Spring Harbor, N.Y.) may be used to construct nucleic acid sequences which encode a monoclonal antibody molecule or antigen binding region thereof.

Antibody molecules may be purified by known techniques, such as for example immunoabsorption or immunoaffinity chromatography, chromatographic methods such as High Performance Liquid Chromatography, or a combination thereof.

Antibody fragments which contain idiotype of the molecule can be generated by known techniques. For example, such fragments include but are not limited to, the $F(ab')_2$ fragment which can be produced by pepsin digestion of the antibody molecule; the Fab' fragments which can be generated by reducing the disulfide bridges of the $F(ab')_2$ fragment, and the 2 Fab or Fab fragments which can be generated by treating the antibody molecule with papain and a reducing agent.

The novel attachment glycoprotein nucleic acid of this invention can be used in methods for serological detection of different avian pneumovirus subtypes, in development of DNA vaccination procedures and the production of subunit vaccines using techniques such as ELISA using the recombinant protein or a peptide of the invention. The present invention, which relates to nucleic acids encoding the APV/CO attachment glycoprotein and to the glycoprotein, peptide fragments, or derivatives produced therefrom, as well as antibodies directed against the attachment glycoprotein and peptides, may be utilized to diagnose APV/CO virus infection. For example, the nucleic acid molecules of the invention may be utilized to detect the presence of APV/CO viral nucleic acid in APV/CO-infected animals by hybridization techniques, including Northern blot analysis, wherein a nucleic acid preparation obtained from an animal is exposed to a potentially complementary nucleic acid molecule of the invention under conditions which allow hybridization to occur and such that hybridization may be detected. For example, but not limited to, total RNA may be prepared from swabs of nasal tissue, tracheal swabs, or isolates from any upper respiratory tract mucosal surface obtained from a bird potentially infected with APV/CO. The RNA may then be subjected to Northern Blot analysis in which detectably labeled oligonucleotide probe derived from APV/CO attachment glycoprotein nucleic acid may be exposed to a Northern Blot filter bearing the poultry RNA under conditions permissive for hybridization; following hybridization, the filter may be washed and binding of probe to the filter may be visualized by autoradiography. Alternatively, if low levels of APV/CO are present in a diagnostic sample, it may be desirable to detect the presence of APV/CO nucleic acid using oligonucleotides of the invention in PCR reaction in order to amplify the amount of virus nucleic acid present.

Additionally, viral RNA amplified from cultured cells may be analyzed for APV/CO sequences by blot hybridization techniques (See, Gilmartin, P. M., Nucleic Acid Hybridization, John Wiley & Sons, LTD., 1995). The presence of APV/CO sequence not provided by the primer in the product of such a PCR reaction would be indicative of APV/CO infection.

In further embodiments, the APV/CO attachment glycoprotein and peptides of the invention may be used in the diagnosis of APV/CO infection. For example, and not by way of limitation, APV/CO attachment protein and peptides may be used in enzyme linked immunosorbent assay (ELISA), immunoprecipitation, rosetting or Western blot techniques to detect the presence of anti-APV/CO antibodies. A rise in titer of anti-APV/Co antibodies may be indicative of active APV/CO infection. A serum sample may be exposed to APV/CO attachment glycoprotein or peptide under conditions permissive for binding of antibody to protein or peptide and such that binding of antibody to protein or peptide may be detected. For example, and not by way of limitation, APV/CO protein or peptide may be immobilized on a solid surface, exposed to serum potentially comprising anti-APV/CO attachment glycoprotein antibody (test serum) under conditions permissive for binding of antibody to protein or peptide, and then exposed to an agent which permits detection of binding of antibody to APV/CO attachment glycoprotein or peptide, for example, a detectably labeled anti-immunoglobulin antibody. Alternatively, APV/CO attachment glycoprotein or peptide may be subjected to Western blot analysis, and then the Western blot may be exposed to the test serum, and binding of antibody to the attachment glycoprotein or peptide may be detected as set forth above. In further, non-limiting embodiments of the invention, APV/CO attachment glycoprotein or peptide may be adsorbed onto the surface of a red blood cell, and such antigen-coated red blood cells may be exposed to serum which potentially contains anti-APV/CO virus antibody. Rosette formation by serum of antigen coated red blood cells may be indicative of APV/CO exposure or active infection.

In addition, antibodies which recognize APV/CO attachment glycoprotein may be utilized in ELISA or Western blot techniques in order to detect the presence of APV/CO attachment glycoprotein, which would be indicative of active APV/CO infection (Langedijk et al., J. Clin. Microbiol., Volume 35, 1656–1660, 1997; Langedijk et al, J. Immunol. Methods, Volume 193, 157–166, 1996). An ELISA method effective for detection of the glycoprotein of the invention can, for example, be as follows: (1) bind the antibody to a substrate; (2) contact the bound antibody with the a sample thought to contain the glycoprotein; (3) contact the antibody-sample with a secondary antibody bound to a detectable moiety such as, for example, horseradish peroxidase or alkaline phosphatase; (4) contact the antibody-sample-detectable moiety with a color reagent; (6) observe a color change.

Another immunologic method that can be used for detecting avian metapneumovirus (Colorado) utilizes monoclonal antibodies (Mabs) for detection of antibodies specifically reactive with avian metapneumovirus (Colorado) antigens. Sample from the test subject is reacted with glycoprotein bound to a substrate (antigen antibody complex) (e.g. 96 well plate). Excess sample is thoroughly washed away. A labeled (enzyme-linked, fluorescent, radioactive, etc.) monoclonal antibody is then reacted with the previously reacted antigen-antibody complex. The amount of inhibition of monoclonal antibody binding is measured relative to a control. The degree of monoclonal antibody inhibition is a very specific test for a particular variety or strain since it is based on monoclonal antibody binding sphericity. Mabs can also be used for detection directly in cells by IFA.

A micro-agglutination test can also be used to detect the presence of avian metapneumovirus (Colorado). Latex beads (or red blood cells) are coated with the antigen and mixed with a sample, such that antibodies in the sample are specifically reactive with the antigen causing agglutination. The agglutinated antigen-antibody complexes form a precipitate, visible to the naked eye or capable of being detected by a spectrophotometer. In a modification of the above test, antibodies specifically reactive with the antigen can be bound to the beads and the antigen in the sample thereby detected.

In addition, as in a typical sandwich technique, the antibody can be bound to a substrate and reacted with antigen. Thereafter, a secondary labeled antibody is bound to epitopes not recognized by the first antibody and the secondary antibody is detected (Hanzari et al., Com. Immunol. Microbiol. Infect. Dis., Volume 25, 59–68, 2002).

In the diagnostic methods taught herein, the glycoprotein can be bound to a substrate and contacted with a sample. This sample can be taken directly from the bird or in a partially purified form. In this manner, antibodies, specific for the antigen (primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with, the ligand or reacted antibody, will be selected for its ability to react with multiple sites on the primary antibody. Thus, for example, several molecules of the secondary antibody can react with each primary antibody, making the primary antibody more detectable.

The detectable moiety will allow visual detection of a precipitate or a color change, visual detection by microscopy, or automated detection by spectrometry, radiometric measurement, or the like. Examples of detectable moieties include fluorescein and rhodamine (for fluorescence microscopy), horseradish peroxidase (for either light or electron microscopy and biochemical detection), biotin-streptavidin (for light or electron microscopy), and alkaline phosphatase (for biochemical detection by color change). The detection methods and moieties used can be selected, for example, from the list above, or other suitable examples by the standard criteria applied to such selections (Harlow and Lane, Antibodies; A Laboratory Manual, Cold Spring Harbor Laboratory, Cold Spring Harbor, N.Y., 1988; herein incorporated by reference).

Since the present invention provides avian metapneumovirus (Colorado) attachment glycoprotein for the detection of infectious avian metapneumovirus, other serological methods such as flow cytometry and immunoprecipitation can also be used as detection methods.

Throughout this application, various publications are referenced. The disclosures of these publications in their entireties are hereby incorporated by reference into this application in order to more fully describe the state of the art to which this invention pertains.

The following examples are intended to further illustrate the invention and are not intended to limit the scope of the invention as defined by the claims.

EXAMPLE 1

Avian Metapneumovirus strain Colorado (MPV/CO/C) (NVSV, APHIS, USDA, Ames, Iowa, USA), avian Minnesota 2a (MPV/MN2a/C), and avian Minnesota 7 (MPV/MN7/C) were propagated in Vero cells. Vero cells were propagated in Minimal Essential Medium (MEM) containing about 5% fetal bovine serum, about 1% 100×antibiotics/antimycotics solution (Ivitrogen, Carlsbad, Calif.) to about 95% confluency. Cells were infected at a multiplicity of infection of about 0.1 (MOI=0.1)adsorbed for about 1 hour at about 37° C. and overlayed with a maintenance media containing MEM, about 2% fetal bovine serum, about 1% 100×antibiotics/antimycotics solution (Invitrogen, Carlsbad, Calif.). Infected cells were incubated at about 37° C., in about 5% $CO_2$ for about 48–72 hours or until about a >90% cytopathic effect (CPE) was observed by light microscopy.

Infected cells (About >90%CPE) were harvested by scraping followed by differential centrifugation. Cell supernatant was clarified by high-speed centrifugation at about 2,000×g for about 20 minutes. Subsequently, virus is purified by centrifugation at about 125,000×g through about 15% Tris buffered (about 10 mM at about pH 7.5) sucrose for about 65 minutes utilizing a Beckman SE28 rotor. The virus pellet is suspended in about 50 μl of about 10 mM Tris at about pH 7.5.

EXAMPLE 2

Total cytoplasmic RNA from APV/Co-infected cells was purified using Rneasy Mini total RNA isolation kit (Qiagen, Valencia, Calif.) according to manufacturer's protocol. Isolated RNA was analyzed in about 1% agarose gels stained with ethidium bromide (about 10 μg/ml) and viewed on a UV-transilluminator for purity of RNA.

Total APV/CO-infected cell RNA was reverse-transcribed (Myers et al., Biochemistry, Volume 30(31) 7661–7666, 1991) followed by polymerase chain reaction amplification (RT-PCR) utilizing APV/CO attachment glycoprotein gene specific primers. Total APV/CO-infected cell RNA was reverse-transcribed using APV G1 primer 5'-AACATGGAGCCCCTGAAAGTCTCT-3', SEQ ID NO: 3 and APV G1306c primer 5'-TTTTTGGTTGTTGCCTGTCTCTT-3', SEQ ID NO: 4 at about 60° C. utilizing thermoscript (Invitrogen). The primers were generated by computer analysis (Primer Design, Scientific & Educational Software, Durham, N.C.). APV/CO attachment glycoprotein gene cDNA was the amplified by polymerase chain reaction (Barnes, PNAS, USA, Volume 91(6), 2216–2220, 1994) for about 35 cycles utilizing primers G1 and G1306Cwith an annealing temperature of about 60° C. A DNA fragment representing the full-length attachment glycoprotein gene was produced following amplification by PCR. The DNA fragment was isolated from an agarose gel using Qiaquick Agarose gel purification kit (Qiagen, Valencia, Calif.) and cloned into PCR-XL Topo cloning vector (Invitrogen, Carlsbad, Calif.) according to manufacturer's protocol. Presence of cloned DNA insert were detected by digestion of the plasmids with the restriction enzyme EcoRI. Double-stranded sequencing with Taq polymerase (Applied Biosystems Inc., Foster City, Calif.) and fluorescent labeled dideoxynucleotides was performed with an automated sequencer. Nucleotide sequence editing, prediction of amino acid sequences, and protein computer structure predictions were completed using Editseq, Megalign, and Protean programs within the Lasergene system (DNASTAR, Inc., Madison, Wis.) and Gene Works 2.3 programs (Intelligenetics, Mountain View, Calif.). Alignments were performed using the CLUSTAL W method (Thompson et al., Nucleic Acids Res., Volume 22(22), 4673–4680, 1994). Nucleotide sequence analysis, including determination of synonymous and nonsynonymous substitutions (Nei et al., Mol. Biol. Evol., Volume 3(5), 418–426, 1986) was completed using the Molecular Evolutionary Genetic Analysis system (MEGA Version 1.01, Kumar et al, The Pennsylvania State University, University Park, Pa.). To determine relationships among avian metapneumovirus isolates and how protein sequence information related to current designations, analysis, was performed by Phylogenetic Analysis Using Parsimony (PAUP) following 2000 bootstrap replications (Hedges, Mol. Biol. Evol., Volume 9(2), 366–369, 1992).

The attachment protein G gene (accession no. AF513020) is about 1,321 based in length, which is about 61 nucleotides longer than the G protein of both avian MPV subgroups A and B (Juhasz et al., J. Gen. Virol., Volume 75 (11), 2873–2880, 1994). The avian MPV/C G gene is about 136 nucleotides long than the avian MPV/D (Bayon-Auboyeret al., J. Gen. virol., Volume 81(11), 2723–2733, 2000)and about 710 nucleotides greater n length than the human MPV (van den Hoogen et al., Nat. Immunol., Volume 2(8), 119–132, 2002). The sequence of the transcription start sequence was identical to the conserved sequences of the other avian MPV genes (Dar et al., Virus Res., Volume 79(102), 15–25, 2001; Li et al., Virus Res., Volume 41(2), 185–191, 1996; Ling et al., J. Gen. Virol., Volume 73(7), 1709–1715, 1992; Seal et al., Virus Res., Volume 66(2), 139–147, 2000) followed by the AUG start codon at nucleotide position 14. There was one major opening reading frame from residues 14–1321, encoding a predicted protein of about 435 amino acids with about a $M_r$ 48,483 and a net charge of about 23.15 at neutral pH. A second putative leader sequence was identified at position 715–723 followed by a second putative open reading frame spanning positions 728–1,321, encoding a predicted protein of about 197 amino acid residues with about a $M_r$ 22,024 and a net charge of about 11.20 at neutral pH.

Analysis of the predicted avian MPV/C G attachment protein by BLAST (Altschul et al., Nucleic Acids Res., Volume 25(17), 3389–3402, 1997) revealed two mucin-like motifs encompassing amino acid positions 21 to 163 and 190 to 433 with potential trans-membrane regions within these areas from residues 24 to 45 and 266 go 287 (See FIG. 1). These highly basic regions are potentially important for heparin binding on the membrane surface of infected cells and play a key role in pneumovirus entry into cells (Feldman et al., J. Virol., Volume 73(8), 6610–6617, 1999). Between the two mucin-like regions is a conserved hydrophobic domain that includes a fractalkine-like chemokine sequence encompassing positions 172 through 176 (FIG. 1). The fractalkine-like chemokine region of human RSV binds to the specific receptor of the chemokine fractalkine. This is a chemokine motif found in the human RSV G protein that may be important in trafficking of pulmonary polymorphic neutrophils (PMNs) and natural killer cells during infection. It may also contribute to altered chemokine mRNA expression of macrophage inflammatory protein 1α(MIP-1α), MIP-1β, MIP-2, monocyte chemoattractant protein 1 and IFN-inducible protein 10 (IP-10) by bronchoalveolar leukocytes (Tripp et al., Nat. Immunol., Volume 2(8), 732–738, 2001).

The G gene nucleotide sequence of avian MPV/Co/C, avian MPV/MN2a/C, avian MPV/MN7/C, avian MPV/A, avian MPV/B, avian MPV/D, human RSV, and bovine RSV were aligned with the combined SH and G gene of the human MPV. The combined SH and G genes of human MPV were included due to similarities in the SH protein with the G protein of other members of the Pneumovirinae. Sequence identities of avian MPV/CO/C gene compared to G genes of other pneumoviruses ranged from about 33.3% to about 98.6% (Table 1). The nucleotide sequence identity of the avian MPV/CO/C and avian MPV/MN2a/C G gene was about 98.6% with about 12 nonsynonymous and 6 synonymous differences (ratio of nonsynonymous/synonymous substitutions of 2). The greater number of nonsynonymous nucleotide substitutions suggests that positive selection has occurred (Ina, Genet., Volume 75, 91–115, 1996) since the time of the isolations made in Colorado relative to viruses isolated more recently in Minnesota. Sequence identity of avian MPV/CO/C and avian MPV/MN7/C was about 86.3%, a similar divergence reported for other genes between these two isolates (Shin et al., J. Clin. Microbiol., Volume 40(5), 1687–1693, 2002). While the nucleotide sequence identity between the G gene of avian MPV/CO/C and the combined SH-G genes of human MPV was 42.5% (Table 1). The sequence identity of avian MPV/CO/C gene with the avian MPV/A, avian MPV/B, avian MPV/D, human RSV, and bovine RSV sequences was 33.3%, 33.3%, 33.4%, 34.0%, and 36.3%, respectively.

The predicted amino acid sequence of APV/CO/C G protein was aligned with other members of the Pneumovirinae and identities ranged from about 4–16.5% when compared with avian MPV/A, avian MPV/B, avian MPV/D, human RSV, bovine RSV, and pneumonia virus of mice. This increased to 97% when compared to the avian MPV/ MN2a/C isolate or 72% for the avian MPV/MN7/C isolate and 21% for the human MPV (combined SH-G protein).

TABLE 1

Nucleotide identity (%) among the cell attachment (g) glycoprotein gene of pneumoviruses.

| | APV/CO/C | APV/MN2a/C | APC/MN7/C | APV/A[a] | APV/B[b] | APV/D[c] | hRSV[d] | bRSV[e] | hMPV[f] |
|---|---|---|---|---|---|---|---|---|---|
| APV/CO/C | — | 98.6 | 86.3 | 33.3 | 33.9 | 34.3 | 34.0 | 36.3 | 42.5 |
| APV/MN2a/C | 98.6 | — | 86.2 | 33.6 | 35.6 | 32.9 | 34.2 | 36.2 | 42.0 |
| APV/MN7/C | 86.3 | 86.2 | — | 34.2 | 34.3 | 34.2 | 36.8 | 37.6 | 43.7 |
| APV/A[a] | 33.3 | 33.6 | 34.2 | — | 48.2 | 51.4 | 38.6 | 42.1 | 38.5 |
| APV/B[b] | 33.9 | 35.6 | 34.3 | 48.2 | — | 44.1 | 35.9 | 33.4 | 42.4 |
| APV/D[c] | 33.4 | 32.9 | 34.2 | 51.4 | 44.1 | — | 44.4 | 43.8 | 43.3 |
| hRSV[e] | 34.0 | 34.3 | 36.8 | 38.6 | 35.9 | 44.4 | — | 58.8 | 44.8 |
| BRSV[f] | 36.2 | 36.2 | 37.6 | 42.1 | 33.4 | 43.8 | 58.8 | — | 45.7 |
| HMPV | 42.5 | 42.0 | 43.7 | 38.5 | 42.4 | 43.3 | 44.8 | 45.7 | — |

[a]APV subgroup A, isolate CVL 14/1
[b]APV subgroup B, isolate 872S
[c]APV subgroup D, isolate Fr/85/2
[d]hRSV wildtype strain B1
[e]bRSV, isolate ATUE51908
[f]hMPV, isolate 00-1, combined SH-G genes The foregoing detailed description is for the purpose of illustration. Such detail is solely for that purpose and those skilled in the art can make variations therein without departing from the spirit an scope of the invention.

We claim:

1. An isolated nucleic acid sequence encoding an open reading frame of an avian pneumovirus (Colorado) Type C strain attachment glycoprotein having a sequence as set forth in SEQ ID NO 1.

2. A vector comprising the nucleic acid of claim 1.

3. A method for detecting avian pneumovirus (Colorado) Type C strain comprising:

(a) isolating total RNA from a sample to be tested,
(b) synthesizing a first strand DNA with SEQ ID NO. 1 from said isolated total RNA using a reverse primer selected from the group consisting of SEQ ID NO 3, SEQ ID NO 4, or mixtures thereof,
(c) amplifying said first strand DNA using a primer from step b to form an amplified product, and
(d) detecting the amplified first strand DNA product of step ( ).

* * * * *